(12) United States Patent
Ishikawa et al.

(10) Patent No.: US 7,416,651 B2
(45) Date of Patent: Aug. 26, 2008

(54) GAS SENSOR

(75) Inventors: Hideki Ishikawa, Aichi (JP); Shoji Kitanoya, Aichi (JP); Takeshi Morita, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 791 days.

(21) Appl. No.: 10/767,180

(22) Filed: Jan. 30, 2004

(65) Prior Publication Data

US 2004/0182705 A1 Sep. 23, 2004

(30) Foreign Application Priority Data

Jan. 31, 2003 (JP) ............................. 2003-024984
Dec. 5, 2003 (JP) ............................. 2003-407825

(51) Int. Cl.
*G01N 27/407* (2006.01)
(52) U.S. Cl. ...................................... 204/425; 204/426
(58) Field of Classification Search .......... 204/424–429
See application file for complete search history.

(56) References Cited

U.S. PATENT DOCUMENTS

| 4,305,803 | A | | 12/1981 | Beyer et al. | |
|---|---|---|---|---|---|
| 4,795,544 | A | * | 1/1989 | Nishizawa et al. | 204/425 |
| 5,322,602 | A | * | 6/1994 | Razaq | 205/788 |
| 5,897,766 | A | * | 4/1999 | Kawatsu | 204/426 |
| 5,958,214 | A | | 9/1999 | Nikolskaja | |
| 6,296,748 | B1 | * | 10/2001 | Ohtsuki et al. | 204/427 |
| 6,506,296 | B2 | * | 1/2003 | Babes-Dornea et al. | 205/775 |
| 6,652,723 | B1 | | 11/2003 | Nadanami et al. | |
| 6,913,677 | B2 | * | 7/2005 | Kitanoya et al. | 204/424 |

FOREIGN PATENT DOCUMENTS

| EP | 0 710 835 A2 | 5/1996 |
|---|---|---|
| EP | 1 103 807 A2 | 5/2001 |
| JP | 2001-215214 A | 8/2001 |

OTHER PUBLICATIONS

European Search Report for EP 04 00 2159 dated May 24, 2004.

* cited by examiner

*Primary Examiner*—Kaj K Olsen
(74) *Attorney, Agent, or Firm*—Sughre Mion, PLLC

(57) ABSTRACT

There is provided a gas sensor for measuring the concentration of a specific gas component in a gas under measurement, including a gas diffusion rate limiting portion, a measurement chamber communicating with an atmosphere of the gas under measurement through the gas diffusion rate limiting portion, a sensor element having an ion-conductive layer with first and second surfaces, a first electrode disposed in contact with the first surface of the ion-conductive layer within the measurement chamber and a second electrode disposed in contact with the second surface of the ion-conductive layer and communicating exclusively with the atmosphere of the gas under measurement and a cylindrical support member installing therein the sensor element with the first and second surfaces of the ion-conductive layer directed toward front and base end sides of the support member, respectively.

19 Claims, 13 Drawing Sheets

FIG.3
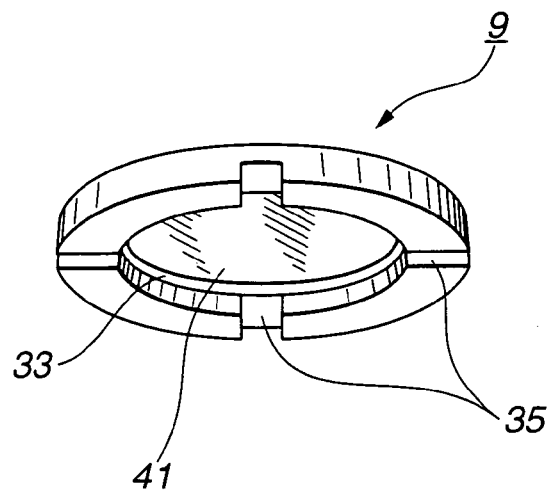
FIG.4A      FIG.4B
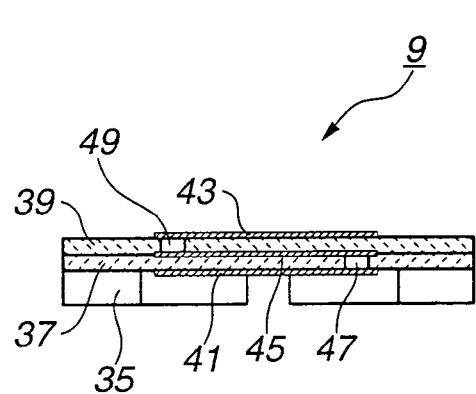      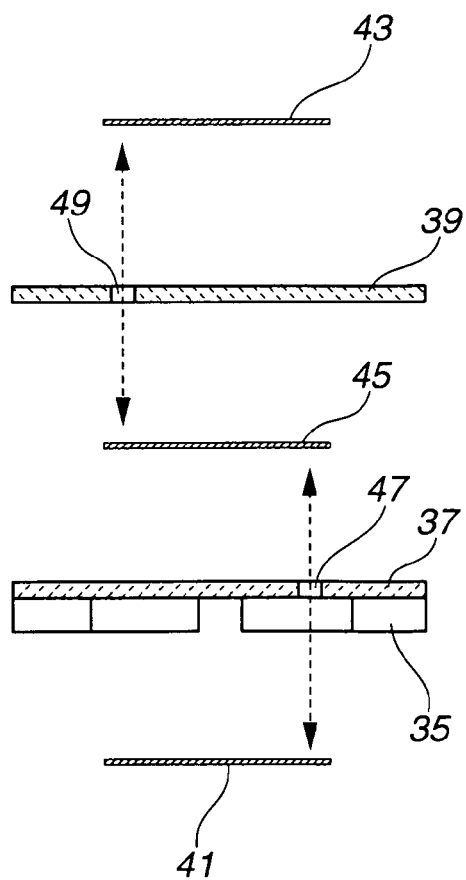

FIG.7A
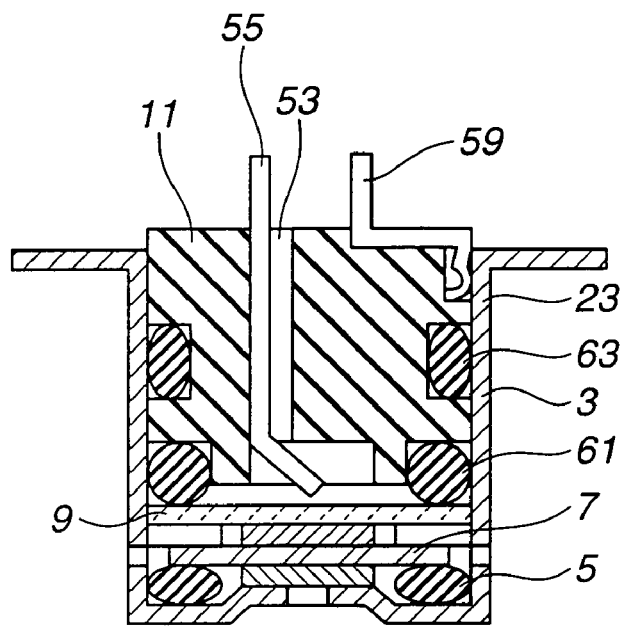
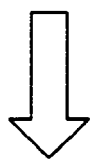
FIG.7B
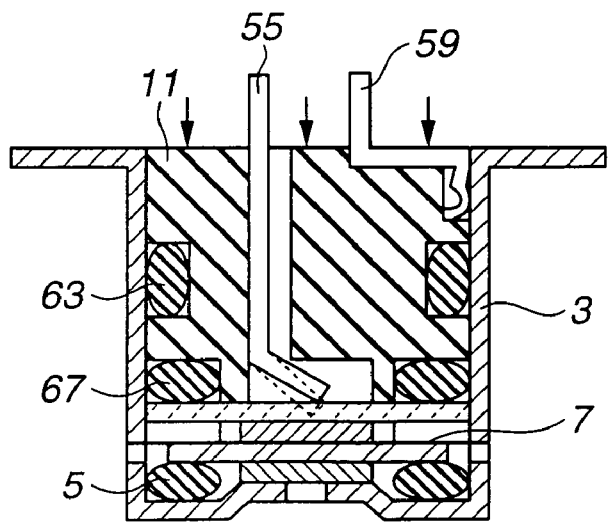
FIG.7C
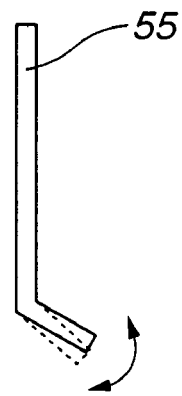

FIG.14A FIG.14B
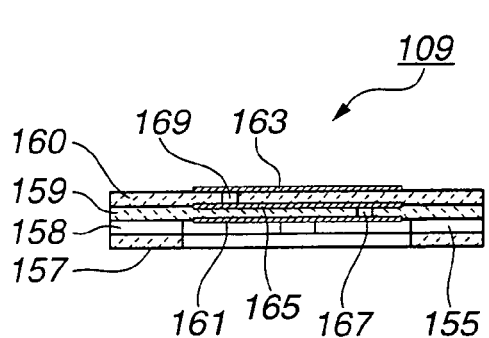
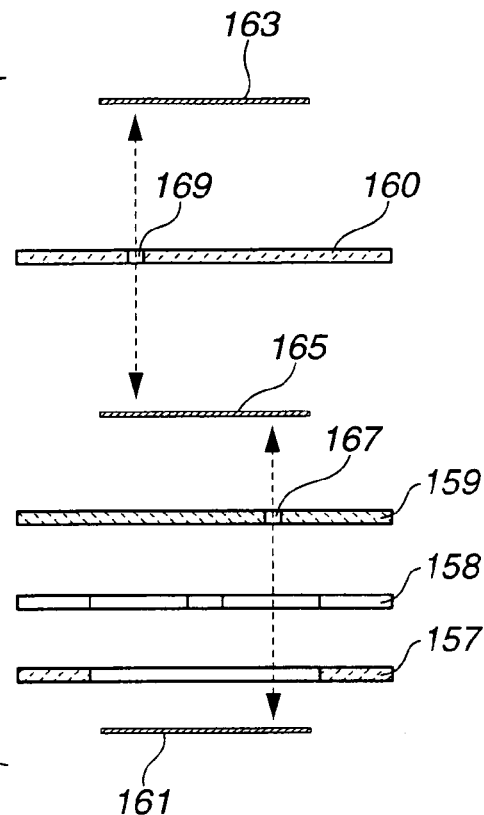
FIG.15A FIG.15B FIG.15C FIG.15D
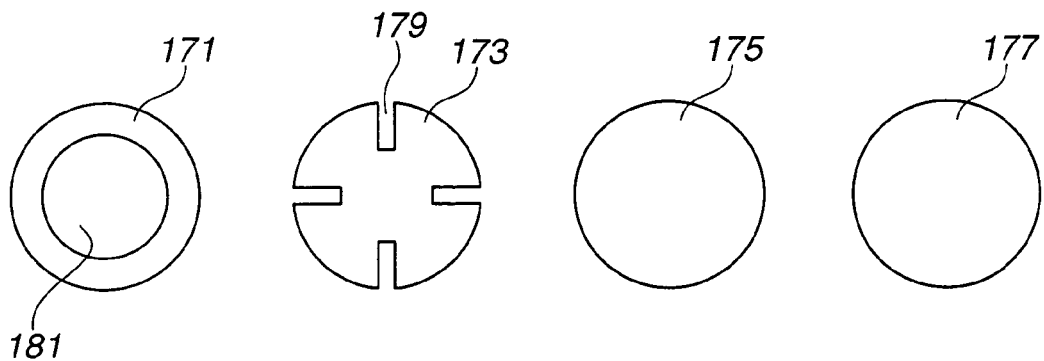

GAS SENSOR

BACKGROUND OF THE INVENTION

The present invention relates to a gas sensor, such as a hydrogen gas sensor for measuring the hydrogen concentration of a fuel gas used in a fuel cell.

With a growing awareness of global-scale environmental deterioration in the recent years, fuel cells have been intensively studied as clean and efficient power sources. Among various fuel cells, a polymer electrolyte fuel cell (PEFC) is expected to be suitable for car and home use owing to its advantageous characteristics, e.g., low-temperature operability and high output density. In the fuel cell, a reformed gas (obtained from natural gas, methanol or the like) is commonly used as a fuel gas. In order to further improve the efficiency and other performance figures of the fuel cell, there is a need to provide a gas sensor capable of directly measuring the concentration of hydrogen in the reformed gas.

Japanese Laid-Open Patent Publication No. 2001-215214 discloses one type of hydrogen gas sensor 1000, which includes a sensor element provided with a proton-conductive layer 1010 and first and second electrodes 1020 and 1030, a pair of support plates 1050 and 1060 and a sensor mount 1070 as shown in FIG. 17. The proton-conductive layer 1010 is made of a polymer electrolyte. The first and second electrodes 1020 and 1030 are arranged on opposite surfaces of the proton-conductive layer 1010. The support plates 1050 and 1060 support therebetween the sensor element and are held at base end sides thereof to the sensor mount 1070. The hydrogen gas sensor 1000 is fixed to a pipe 1080 to measure the concentration of hydrogen in a gas under measurement flowing through the pipe 1080.

SUMMARY OF THE INVENTION

To fix the hydrogen gas sensor 1000 to the pipe 1080, the sensor mount 1070 could conceivably be mounted on the pipe 1080 in such a manner that the support plates 1050 and 1060 are oriented in a direction perpendicular to an axial direction of the pipe 1080. In such a case, however, the hydrogen gas sensor 1000 becomes susceptible to vibration and impact because each of the support plates 1050 and 1060 is held at one end and hangs free at the other end. It is thus required to provide higher vibration and impact resistance in the hydrogen gas sensor 1000. It is also required to prevent leakage of the gas from the inside of the hydrogen gas sensor 1000 to the outside of the pipe 1080.

In view of the foregoing, it is an object of the present invention to provide a gas sensor having improved vibration and impact resistance and being capable of, when fixed to e.g. a pipe through which a gas under measurement flows, preventing the gas from leaking to the outside of the pipe.

According to a first aspect of the invention, there is provided a gas sensor for measuring the concentration of a specific gas component in a gas under measurement, comprising: a gas diffusion rate limiting portion limiting the rate of diffusion of the gas under measurement; a measurement chamber communicating with an atmosphere of the gas under measurement through the gas diffusion rate limiting portion; a sensor element having an ion-conductive layer with first and second surfaces, a first electrode disposed in contact with the first surface of the ion-conductive layer within the measurement chamber, and a second electrode disposed in contact with the second surface of the ion-conductive layer and communicating exclusively with the atmosphere of the gas under measurement; a cylindrical support member installing therein the sensor element with the first and second surfaces of the ion-conductive layer directed toward front and base end sides of the support member, respectively; and a circuit for applying a voltage between the first and second electrodes to cause dissociation, decomposition or reaction of the specific gas component of the gas in the measurement chamber and thereby generates ions at the first electrode, allowing an electric current flow due to migration of the ions from the first electrode to the second electrode through the ion-conductive layer, and determining the concentration of the specific component in the gas under measurement based on the electric current flow.

According to a second aspect of the invention, there is provided a gas sensor for measuring the concentration of a specific gas component in a gas under measurement, comprising: a gas diffusion rate limiting portion limiting the rate of diffusion of the gas under measurement; a measurement chamber communicating with an atmosphere of the gas under measurement through the gas diffusion limiting portion; a sensor element provided with an ion-conductive layer having first and second surfaces directed to front and base ends of the gas sensor, respectively, a first electrode disposed in contact with the first surface of the ion-conductive layer within the measurement chamber, and a second electrode disposed in contact with the second surface of the ion-conductive layer and communicating exclusively with the atmosphere of the gas under measurement: first and second support members located on front and base end sides of the sensor element, respectively, to support the sensor element between the first and second support members; and a circuit for applying a voltage between the first and second electrodes to cause dissociation, decomposition or reaction of the specific component of the gas in the measurement chamber and thereby generate ions at the first electrode, allowing an electric current flow due to migration of the ions from the first electrode to the second electrode through the ion-conductive layer, and determining the concentration of the specific component in the gas under measurement based on the electric current flow.

According to a third aspect of the invention, there is provided a gas sensor for measuring the concentration of a specific gas component in a gas under measurement, comprising: a gas diffusion rate limiting portion limiting the rate of diffusion of the gas under measurement; a measurement chamber communicating with an atmosphere of the gas under measurement through the gas diffusion limiting portion; a sensor element having an ion-conductive layer with first and second surfaces, a first electrode disposed in contact with the first surface of the ion-conductive layer within the measurement chamber, and a second electrode disposed in contact with the second surface of the ion-conductive layer and communicating exclusively with the atmosphere of the gas under measurement: means for supporting the sensor element in such a manner the first and second surface of the ion-conductive layer are directed toward front and base ends of the gas sensor, respectively; and a circuit for applying a voltage between the first and second electrodes to cause dissociation, decomposition or reaction of the specific component of the gas in the measurement chamber and thereby generate ions at the first electrode, allowing an electric current flow due to migration of the ions from the first electrode to the second electrode through the ion-conductive layer, and determining the concentration of the specific component in the gas under measurement based on the electric current flow The other objects and features of the invention will also become understood from the following description.

BRIEF DESCRIPTION OF THE DRAWINGS

FIG. 3 is a perspective view of a second support member of the gas sensor according to the first embodiment of the present invention.

FIG. 4A is a section view of the second support member of the gas sensor according to the first embodiment of the present invention.

FIG. 4B is an exploded section view of the second support member of the gas sensor according to the first embodiment of the present invention.

FIG. 7A to 7C are schematic views of how to assemble the sensor body according to the first embodiment of the present invention.

FIG. 14A is a section view of the second support member of the gas sensor according to the second embodiment of the present invention.

FIG. 14B is an exploded section view of the second support member of the gas sensor according to the second embodiment of the present invention.

FIG. 15A to 15D are plain views of first to fourth layers of a second support member of the gas sensor according a modification of the second embodiment of the present invention, respectively.

DESCRIPTION OF THE EMBODIMENTS

The present invention will be explained below in detail with reference to the drawings. Although the present invention can be applied to any type of gas sensor for measuring the concentration of a target gas component in a gas under measurement (such as a hydrogen gas sensor or a CO gas sensor), the following first and second embodiments specifically refer to hydrogen gas sensors for measuring the hydrogen concentrations of fuel gases used in polymer electrolyte fuel cells (PEFC) by way of example only.

First Embodiment

Figure 5:
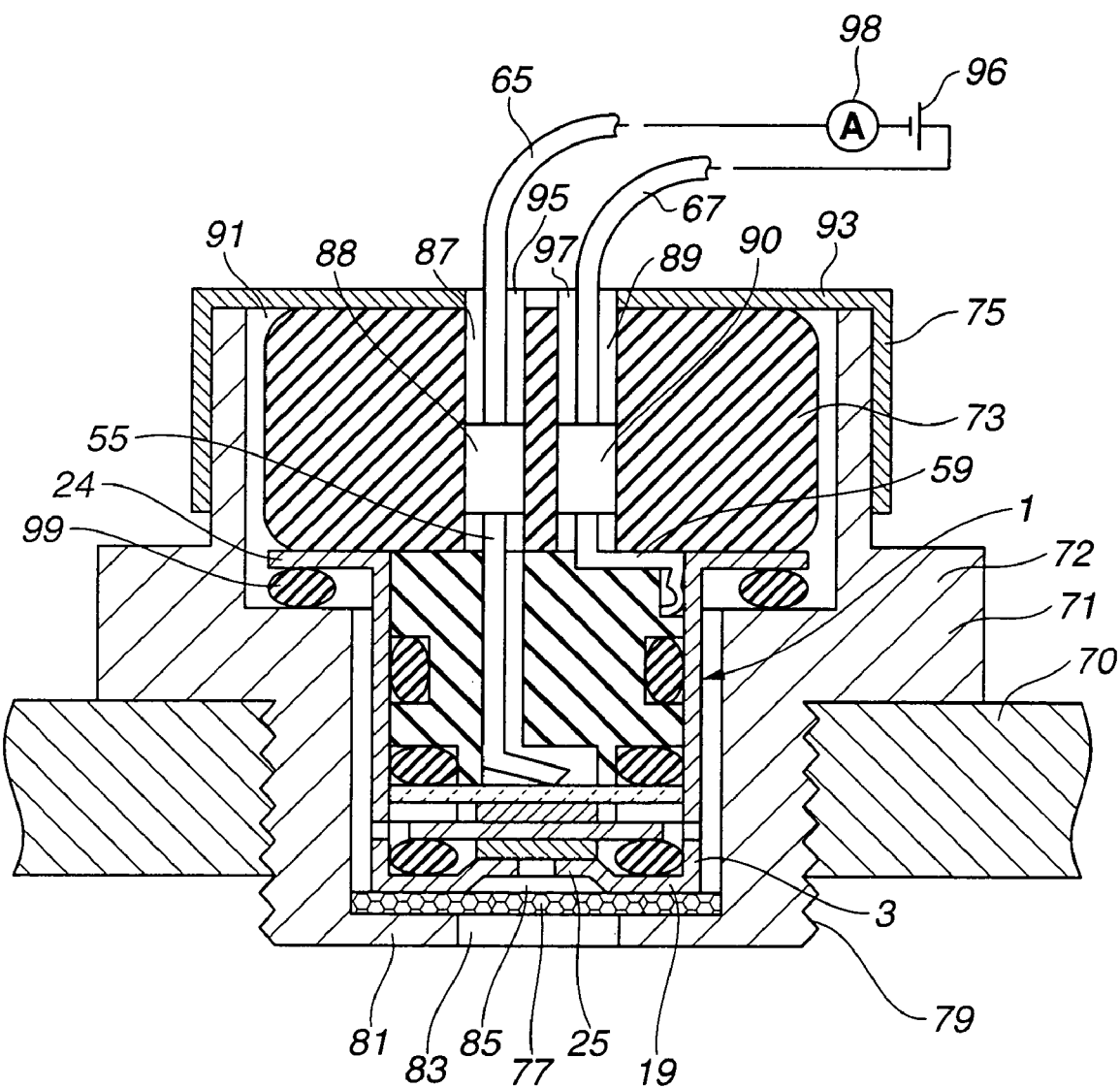
FIG. 5 is a section view of the gas sensor according to the first embodiment of the present invention.

The hydrogen gas sensor of the first embodiment has axially opposite front and base ends, and is designed to be attached to a pipe 70 through which the gas under measurement flows in such a manner that the front end of the hydrogen gas sensor is exposed to the atmosphere of the gas under measurement and that the base end of the hydrogen gas sensor is located outside the atmosphere of the gas under measurement (see FIG. 5).

Figure 1:
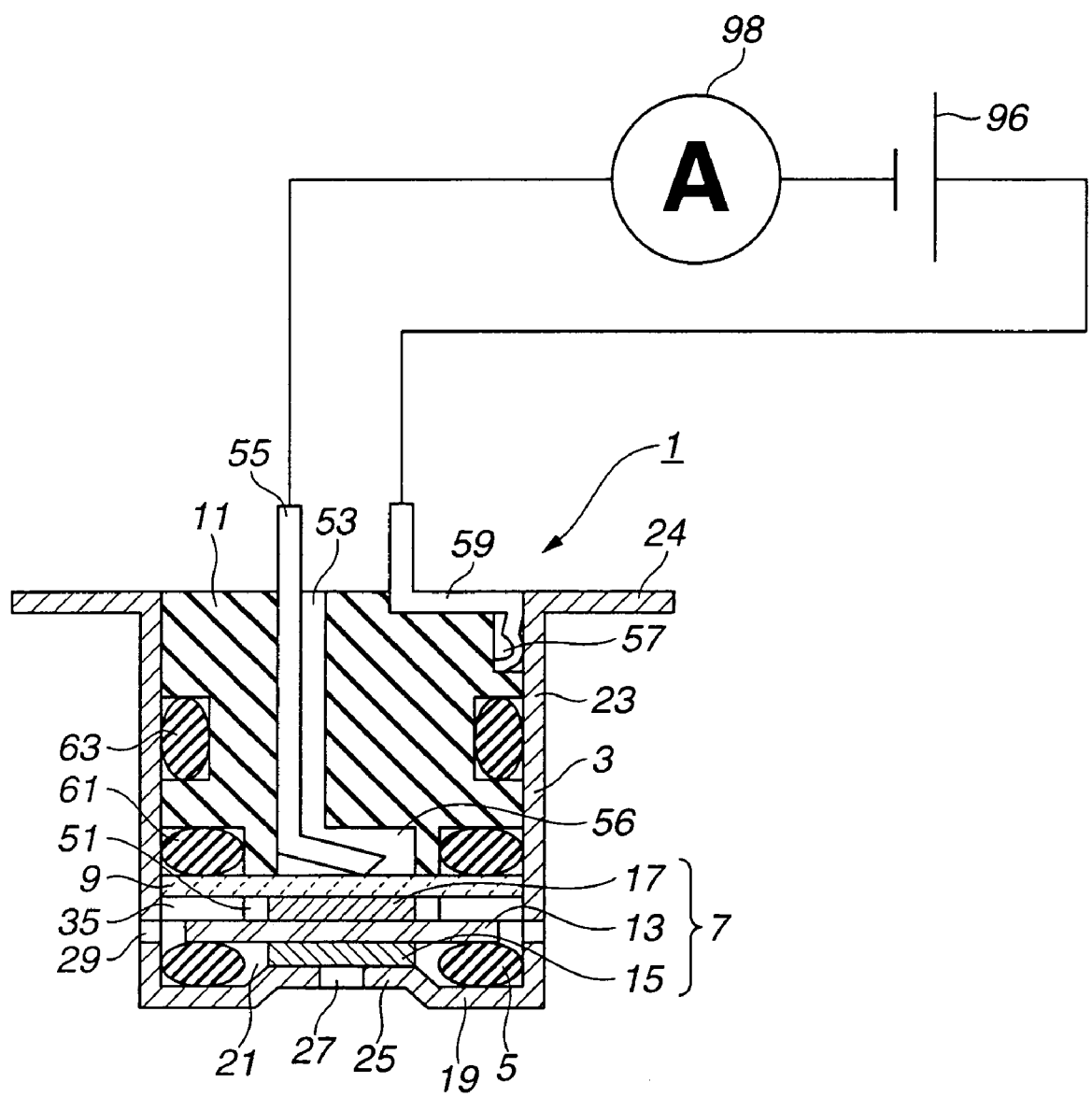
FIG. 1 is a section view of a sensor body of a gas sensor according to a first embodiment of the present invention.
Figure 2:
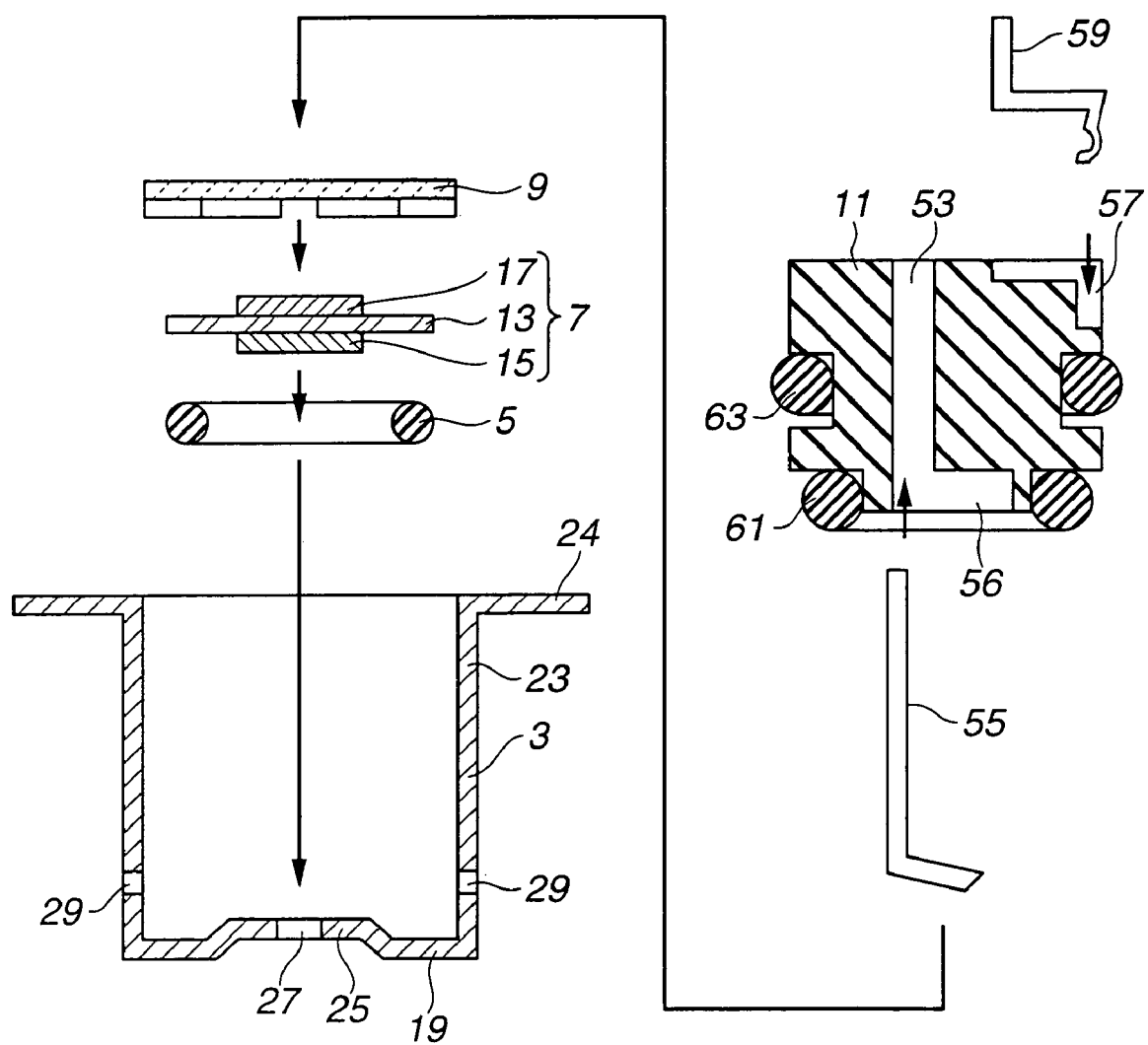
FIG. 2 is an exploded section view of the sensor body of the gas sensor according to the first embodiment of the present invention.

As shown in FIGS. 1 and 2, the hydrogen gas sensor includes a substantially cylindrical sensor body 1 provided with a sensor element 7, first and second support members 3 and 9, O-rings 5, 61 and 63, a spacer 11 and a pair of negative and positive terminals 55 and 59 to measure the concentration of hydrogen in the gas under measurement.

The first support member 3 is made of a metal, such stainless steel. Further, the first support member 3 is formed into a substantially bottomed-cylindrical casing and has a bottom 19 at a front end side thereof, a cylindrical wall 23 and a flange 24 extending at a base end side thereof radially outwardly from the cylindrical wall 23, so that the O-ring 5, the sensor element 7, the support member 9 and the spacer 11 are placed in the support member 3 in order of mention (from the front end side) along an axial direction of the support member 3. Alternatively, the first support member 3 may be formed so as to install therein at least the sensor element 7. A center portion 25 of the bottom 19 is protruded toward the inside of the support member 3 (i.e. toward the base end side).

The sensor element 7 includes a disc-shaped proton-conductive layer 13 having opposite first and second surfaces and disc-shaped first and second electrodes 15 and 17 disposed in contact with the first and second surfaces of the proton-conductive layer 13, respectively. The proton-conductive layer 13 permits the migration of protons (H+) therethrough from one surface to the other surface, e.g., from the first surface to the second surface by a pumping action. Desirably, the proton-conductive layer 13 is made of a material operatable at relatively low temperatures (e.g. 150° C. or lower). A specific example of the material of the proton-conductive layer 13 is a fluorocarbon resin available under the DuPont registered trade name of "NAFION". Each of the first and second electrodes 15 and 17 is a porous electrode containing carbon as a main ingredient. Catalyst layers of e.g. platinum (not shown) are applied to surfaces of the respective first and second electrodes 15 and 17 in contact with the proton-conductive layer 13. The sensor element 7 is installed in the support member 3, with the first and second surfaces of the proton-conductive layer 13 directed toward the front and base end sides of the support member 3, respectively, and with the first electrode 15 brought into contact with the protruded center portion 25 of the bottom 19 of the support member 3.

The O-ring 5 is made of fluoro rubber and held between an outer edge portion of the first surface of the proton-conductive layer 13 and an outer edge portion of the bottom 19 of the support member 3 so as to provide a gas seal between the front end side of the sensor element 7 and the bottom 19 of the support member 3.

With such an arrangement, a measurement chamber 21 enclosing therein the first electrode 15 is defined by the front end side of the sensor element 7, the bottom 19 of the support member 3 and the O-ring 5. A gas introduction hole 27 is formed through the center of the protruded portion 25 of the bottom 19 of the support member 3. The measurement chamber 21 thus communicates with the atmosphere of the gas under measurement, i.e., the inside of the pipe 70 through the gas introduction hole 27. In the first embodiment, the gas introduction hole 27 functions as a gas diffusion rate limiting portion for limiting the rate of diffusion of the gas under measurement.

As shown in FIGS. 3, 4A and 4B, the second support member 9 is mainly made of a ceramic material and formed into a substantially cylindrical plate. More specifically, the second support member 9 includes a disc-shaped first layer 37 having a cylindrically recessed portion 33 formed in a front end side thereof, a disc-shaped second layer 39 laminated to a base end side of the first layer 37, a disc-shaped front end electrode 41 arranged in the recessed portion 33 of the first layer 37, a disc-shaped base end electrode 43 arranged on a base end side of the second layer 39 and an electronically conductive layer 45 arranged between the first and second layers 37 and 39. The first and second layers 37 and 39 are made of ceramic, such as alumina. Each of the front end electrode 41, the base end electrode 43 and the conducive layer 45 are formed by e.g. applying a paste of platinum and alumina and then sintering the applied paste. Through holes 47 and 49 are formed in the first and second layers 37 and 39, respectively, so as to allow an offset therebetween (i.e., to allow axes of the through holes 47 and 49 to become shifted from each other). Inner surfaces of the through holes 47 and 49 are plated with an electrically conductive metal (such as platinum), thereby establishing electrical connections between the front end electrode 41 and the conductive layer 45 and between the conductive layer 45 and the base end electrode 43, respectively. The second support member 9 is disposed on the base end side of the sensor element 7, with the second electrode 17 placed in the recessed portion 33 of the support member 9 and brought into contact with the front end electrode 41 of the support member 9.

With this arrangement, a discharge chamber 51 enclosing therein the second electrode 17 is defined between the front end side of the support member 9 and the base end side of the sensor element 7. Four gas return channel 35 are formed, by cutting, in the front end side of the first layer 37 so as to be opened at the front end side of the second support member 9 and to extend radially outwardly (i.e. in a direction perpendicular to a thickness direction of the support member 9) from the recessed portion 33 at locations 90 degrees apart from each other. Further, a pair of radially opposed gas return holes 29 is formed in the cylindrical wall 23 of the support member 3 at locations corresponding to the proton-conductive layer 13. The discharge chamber 51 thus communicates with the outside of the support member 3, i.e., the atmosphere of the gas under measurement through the gas return channels 35, a clearance between the support member 3 and the outer circumferential portion of the sensor element 7 and the gas return holes 29.

The spacer 11 is made of a material having low elasticity and electrical insulation property, such as a resin or ceramic material. An axial hole 53 is formed through a substantially center portion of the spacer 11, and a cut 56 is formed in a front end side of the spacer 11 so as to extend radially from the hole 53. Also, a generally L-shaped cut 57 is formed in an outer edge portion of a base end side of the spacer 11.

Both of the negative and positive terminals 55 and 59 are made of metal having elasticity, such as stainless steel. The negative terminal 55 is formed into a substantially L-shaped plate and passed through the hole 53 of the spacer 11. A front end portion of the negative terminal 55 is arranged in the cut 56 of the spacer 11 and pressed against the base end electrode 43 of the support member 9 under its elasticity to establish an electrical connection between the base end electrode 43 of the support member 9 and the negative terminal 55. On the other hand, the positive terminal 59 is formed into a crank-shaped plate and arranged in the cut 57 of the spacer 11. A curved front end portion of the positive terminal 59 is pressed against an inner surface of the cylindrical wall 23 of the support member 3 under its elasticity to establish an electrical connection between the cylindrical wall 23 of the support member 3 and the positive terminal 59.

The O-ring 61 is held between the base end side of the support member 9 and the front end side of the spacer 11 to provide a gas seal between the support member 9 and the spacer 11, while the O-ring 63 is held between an outer circumferential surface of the spacer 11 and the inner surface of the cylindrical wall 23 of the support member 3 to provide a gas seal between the spacer 11 and the support member 3. In the first embodiment, the O-rings 61 and 63 are also made of fluoro rubber.

As shown in FIG. 5, the hydrogen gas sensor further includes a metallic sensor housing 71 installing therein the sensor body 1, a grommet 73 pressed against a base end side of the sensor body 1 to hold the sensor body 1 into the sensor housing 71, a metallic cover 75 fitted onto the sensor housing 71, a filter 77 arranged at a front end side the sensor body 1 and sandwiched between the sensor body 1 and the sensor housing 71, a pair of leads 65 and 67 connecting the negative and positive terminals 55 and 59 to a direct-current power source (e.g. battery) 96 via an ammeter 98 and a O-ring 99.

Figure 6:
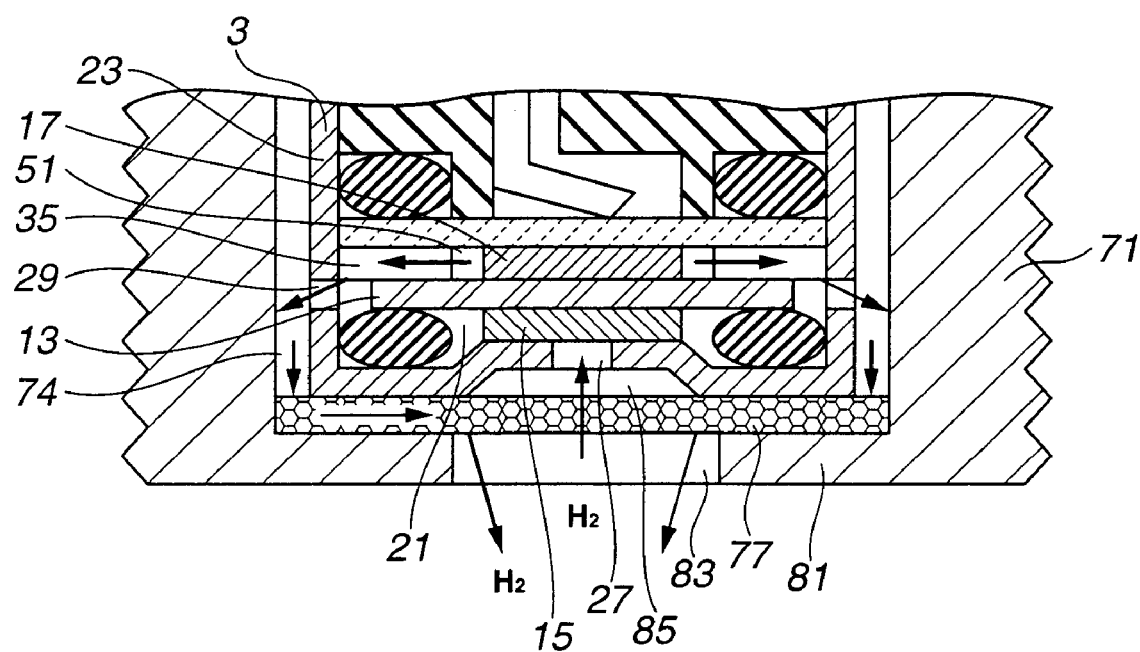
FIG. 6 is a schematic view of how a gas under measurement flows through the gas sensor according to the first embodiment of the present invention.

The sensor housing 71 is formed into a bottomed-cylindrical shape and has a bottom 81 at a front end side thereof, an opening 91 at a base end side thereof, a threaded sensor mount 79 formed on an outer cylindrical surface of the sensor housing 71 for mounting onto the pipe 70 and a flange 72 extending radially outwardly from the axial center of the outer cylindrical surface of the sensor housing 71. A gas port 83 is formed through the bottom 81 so as to introduce the gas under measurement to the sensor body 1. There is an axial space 74 (hereinafter referred to as a gas return channel) left between an inner cylindrical surface of the sensor housing 71 and an outer surface of the cylindrical wall 23 of the support member 3, as shown in FIG. 6.

The filter 77 is made of a fluorocarbon resin having water repellency and air permeability available under the trade name of e.g. "GORE-TEX", and is held between the bottom 19 of the support member 3 and the bottom 81 of the sensor housing 71 so as to cover the whole of the base end side of the bottom 81 including the gas port 83 and be located between the gas introduction hole (gas diffusion rate limiting portion) 27 and the atmosphere of the gas under measurement. There is a space 85 (hereinafter referred to as a buffering chamber) left between the filter 77 and the protruded portion 25 of the bottom 19 of the support member 3. The buffering chamber 85 has a volume of 10.5 mm$^3$ in the first embodiment.

The grommet 73 is made of an elastic material, such as silicone rubber, and pressed against a base end side of the spacer 11 so as to push the support member 9 and the sensor element 7 to the support member 3. A pair of axial holes 87 and 89 is formed through a center portion of the grommet 73 so that base end portions of the negative and positive terminals 55 and 50 comes in the holes 87 and 89, respectively.

The leads 65 and 67 are integrally joined at joints 88 and 90 to the negative and positive terminals 55 and 59, respectively, by caulking or welding.

The cover 75 is shaped into a cylindrical lid with a top 93, and fitted onto the base end side of the sensor housing 71 to close the opening 91 while installing the sensor body 1, the grommet 73 and the other sensor components in the sensor housing 71. Then, the cover 75 is integrally joined to the sensor housing 71 by caulking or welding. A pair of holes 95 and 97 is formed through the top 93 of the cover 75 such that the leads 65 and 67 are inserted through the hole 95 and 97, respectively.

The O-ring 99 is held between the flange 24 of the support member 3 and an inner stepped surface of the sensor housing 71 to provide a gas seal between the support member 3 and the sensor housing 71 and thereby prevent the gas from leaking to the base end side of the sensor housing 71. The O-ring 99 is also made of fluoro rubber in the first embodiment.

The above-explained hydrogen gas sensor operates as follows.

Upon the electrical contact between the positive terminal 59 and the cylindrical wall 23 of the support member 3, the electrical contact between the protruded portion 25 of the support member 3 and the first electrode 15, the electrical contact between the second electrode 17 and the front end electrode 41 of the support member 9 and the electrical contact between the base end electrode 43 of the support member 9 and the negative terminal 55, the hydrogen gas sensor establishes an electric circuit for applying a direct-current voltage of e.g. 250 mV between the first and second electrodes 15 and 17 through the negative and positive terminals 55 and 59 by means of the power source 96.

As shown in FIG. 6, the gas under measurement flows from the inside of the pipe 70 into the measurement chamber 21 through the gas port 83 of the bottom 81 of the sensor housing 71, the filter 77, the buffering chamber 85, and the gas introduction hole 27 of the bottom 19 of the support member 3. By the application of the voltage between the first and second electrodes 15 and 17, hydrogen in the gas under measurement undergoes dissociation, decomposition or reaction within the measurement chamber 21 to generate protons ($H^+$) at the first electrode 15. The generated protons migrate from the first electrode 15 to the second electrode 17 through the proton-conductive layer 13 by the pumping action.

The migration of the protons from the first electrode 15 to the second electrode 17 through the proton-conductive layer 13 causes the flow of an electric current (such as limiting current). The ammeter 98 reads the amount of such an electric current so that the hydrogen gas sensor determines the concentration of hydrogen in the gas under measurement according to the electric current amount read by the ammeter 98.

The protons, drawn to the second electrode 17, are converted into a return gas (i.e. hydrogen) in the discharge chamber 51. The return gas flows through the gas return channel 35 of the support member 9 and the gas return holes 29 of the support member 3 and becomes discharged out of the support member 3. Then, the return gas flows through the gas return channel 74 to the front end side of the support member 3, passes laterally across the filter 77 and returns to the pipe 70 through the gas port 83.

The hydrogen gas sensor of the first embodiment can be assembled by the following procedure.

Firstly, the O-ring 5, the sensor element 7, the support member 9, the O-ring 61, the spacer 11 with the O-ring 63 fitted thereon and the positive terminal 59 are sequentially installed into the support member 3 in order of mention as shown in FIG. 7A. In advance of installing the spacer 11 into the support member 3, the negative terminal 55 is inserted into the hole 53 of the spacer 11 from the front end side. When the spacer 11 is pushed toward the front end side and placed in position within the support member 3, the front end portion of the negative terminal 55 becomes brought into contact with the support member 9 and curved into a substantially L-shape as shown in FIGS. 7B and 7C. This allows proper electrical contact between the negative terminal 55 and the base end electrode 43 of the support member 9 and proper electrical contact between the positive terminal 59 and the cylindrical wall 23 of the support member 3.

Figure 8:
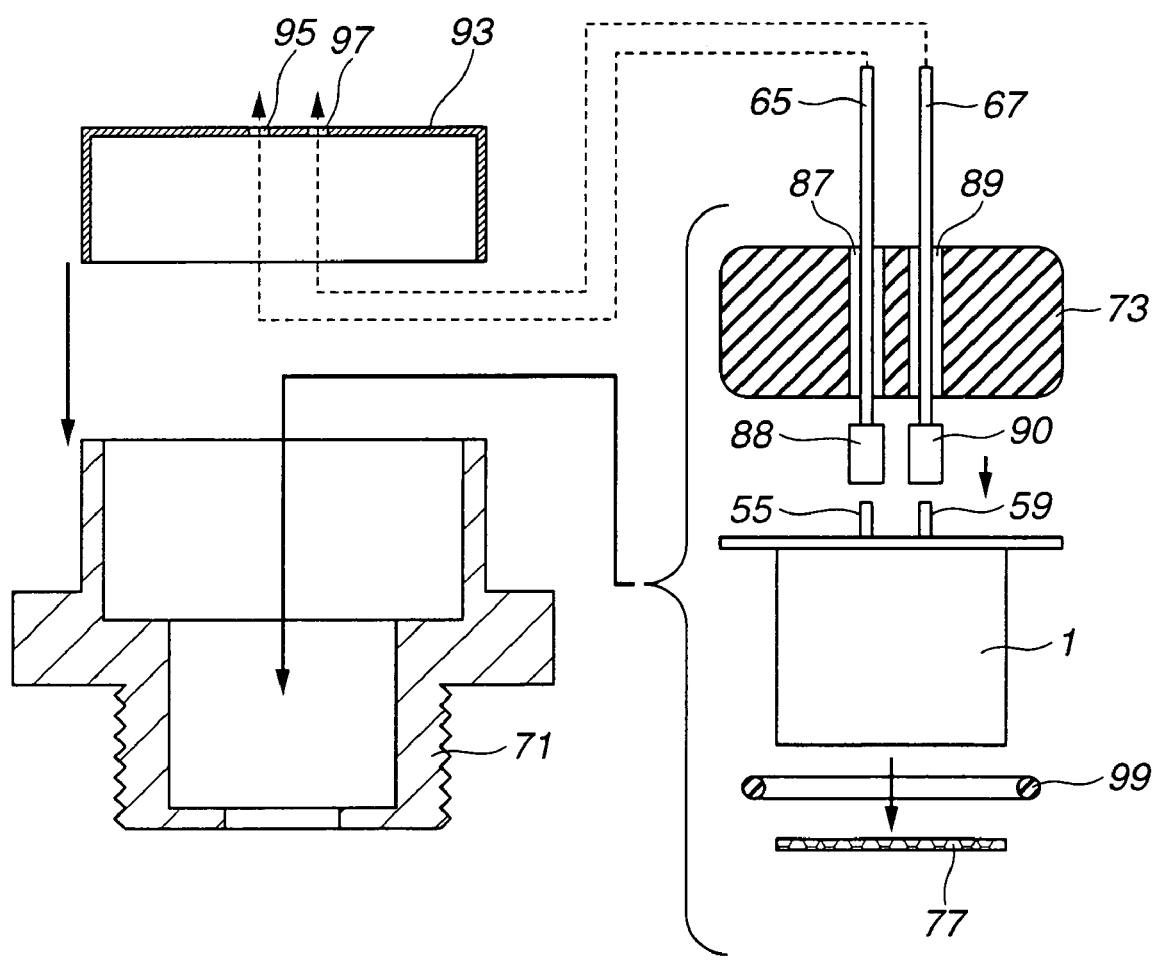
FIG. 8 is a schematic view of how to assemble the gas sensor according to the first embodiment of the present invention.

Then, the filter 77, the O-ring 99, the sensor body 1, the leads 65 and 67 with the respective joints 88 and 90 and the grommet 73 are installed in the sensor housing 71 in order of mention and closed with the cover 93 as shown in FIG. 8. The leads 65 and 67 are connected to the negative and positive terminals 55 and 59 via the joints 88 and 90, respectively, before inserted into the holes 87 and 87 of the grommet 73.

Finally, the cover 93 is joined to the outer cylindrical surface of the sensor housing 71 by caulking or welding, thereby completing the hydrogen gas sensor.

The first embodiment thus provides the following effects.

The sensor element 7 is supported on the bottom 19 of the support member 3 with the first and second surfaces of the proton-conductive layer 13 directed toward the front and base end sides of the support member 3, respectively. Namely, the plate-shaped sensor element 7 is oriented in a direction substantially perpendicular to the axial directions of the cylindrical-shaped support member 3 and of the hydrogen gas sensor and parallel to the axial direction of the pipe 70. The hydrogen gas sensor of the first embodiment is therefore able to attain higher vibration and impact resistance than that of a conventional one-side-supported gas sensor.

Further, the sensor body 1 can be easily assembled by sequentially installing the sensor components, such as the sensor element 7 and the spacer 11, into the support member 3 and becomes compact in size.

The gas introduction passage of the hydrogen gas sensor for introducing the gas from the atmosphere of the gas under measurement into the measurement chamber 21 is defined by the gas port 83 and the gas introduction hole 27. As the gas port 83 and the gas introduction hole 27 are formed in the front end sides of the sensor housing 71 and the support member 3, respectively, at coaxial positions, the gas introduction passage extends axially straight and leads to the measurement chamber 21 from the front end side of the first support member 3 so as to introduce the gas into the measurement chamber 21 from the front end side of the first support member 3. Also, the gas introduction hole 29 formed in the support member 3 functions as the gas diffusion rate limiting portion. Such a simple gas introduction passage allows the efficient introduction of the gas into the measurement chamber 21 as well as the simplification of the front end portion of the hydrogen gas sensor.

On the other hand, the gas return passage of the hydrogen gas sensor for returning the gas to the atmosphere of the gas under measurement is defined by the discharge chamber 51, the gas return channels 35, the gas return holes 29, the gas return channel 74 and the gas port 83. As the gas return channels 35 extend radially outwardly toward the lateral side of the support member 9 and the gas return channel 74 extends axially toward the front end side of the support member 3, the gas return passage extends to the front end side of the first support member 3 so as to return the gas to the atmosphere of the gas under measurement from the front end side of the support member 3. The gas return passage thus becomes simplified as compared to the case where the gas is ejected from the base end of the hydrogen gas sensor and returned to the atmosphere of the gas under measurement from the base end of the hydrogen gas sensor. This simple gas return passage allows the ease of assembly of the hydrogen gas sensor while preventing the leakage of the gas into the outside of the pipe 70 assuredly.

In the above gas introduction and return structures, the gas is introduced from the front end side of the support member 3 and returned to the front end side of the support member 3. It is therefore possible to avoid the entry of condensed water droplets etc. into the inside of the hydrogen gas sensor through the gas introduction hole 27 and the gas return channel 74 and to prevent the gas diffusion rate limiting portion 27 from becoming clogged with the water droplets, by simply disposing the water-repellent filter 77 at the front end side of the support member 3.

Furthermore, the second support member 9 has a laminated structure of the first and second ceramic layers 37 and 39 with the front and base end electrodes 41 and 43, the conductive layer 45 and the through holes 47 and 49. The through holes 47 and 49 for the respective electrical connections between the front end electrode 41 and the conductive layer 45 and between the conductive layer 45 and the base end electrode 43 are radially offset with respect to each other. With such an offset between the through holes 47 and 49, the return gas drawn to the second electrode 17 can be prevented from flowing in a thickness direction of the support member 9 (i.e. toward the base end side) and leaking to the outside of the pipe 70 from the base end of the hydrogen gas sensor. Also, the electrically conductive portion (including the front and base end electrodes 41 and 43, the conductive layer 45 and the though holes 47 and 49) formed on and through the above laminate-structured support member 9 allows easy and proper electrical connection of the second electrode 17 to the external power source 96 through the negative terminal 55.

As the metallic support member 3 has electrical conductivity, the support member 3 in itself provides easy and proper electrical connection of the first electrode 15 to the power source 96 through the positive terminal 59.

In addition, the grommet 73 is pressed against the sensor body 1 to push the spacer 11, the support member 9, the sensor element 7 and the other sensor components toward the front end side. Because of the elasticity of the grommet 73, it becomes possible accommodate dimensional tolerances between such sensor components and absorb expansion and contraction of the sensor components caused under their environmental conditions (such as heat and humidity).

The buffering chamber 85 is left between the gas introduction hole 27 and the filter 77 so as to buffer pressure variations in the gas under measurement to be introduced into the gas introduction hole 27, thereby allowing the filter 77 to exert an effective influence on the gas diffusion in the gas introduction hole 27. The hydrogen gas sensor of the first embodiment is thus able to measure the hydrogen concentration accurately.

Second Embodiment

The second embodiment is structurally similar to the first embodiment. Thus, like parts and portions are designated by like reference numerals in the first and second embodiments to thereby omit repeated descriptions thereof.

The hydrogen gas sensor of the second embodiment also has axially opposite front and base ends and is designed to be attached to a pipe (not shown) through which the gas under measurement flows in such a manner that the front end of the hydrogen gas sensor is exposed to the atmosphere of the gas under measurement and that the base end of the hydrogen gas sensor is located outside the atmosphere of the gas under measurement.

Figure 9:
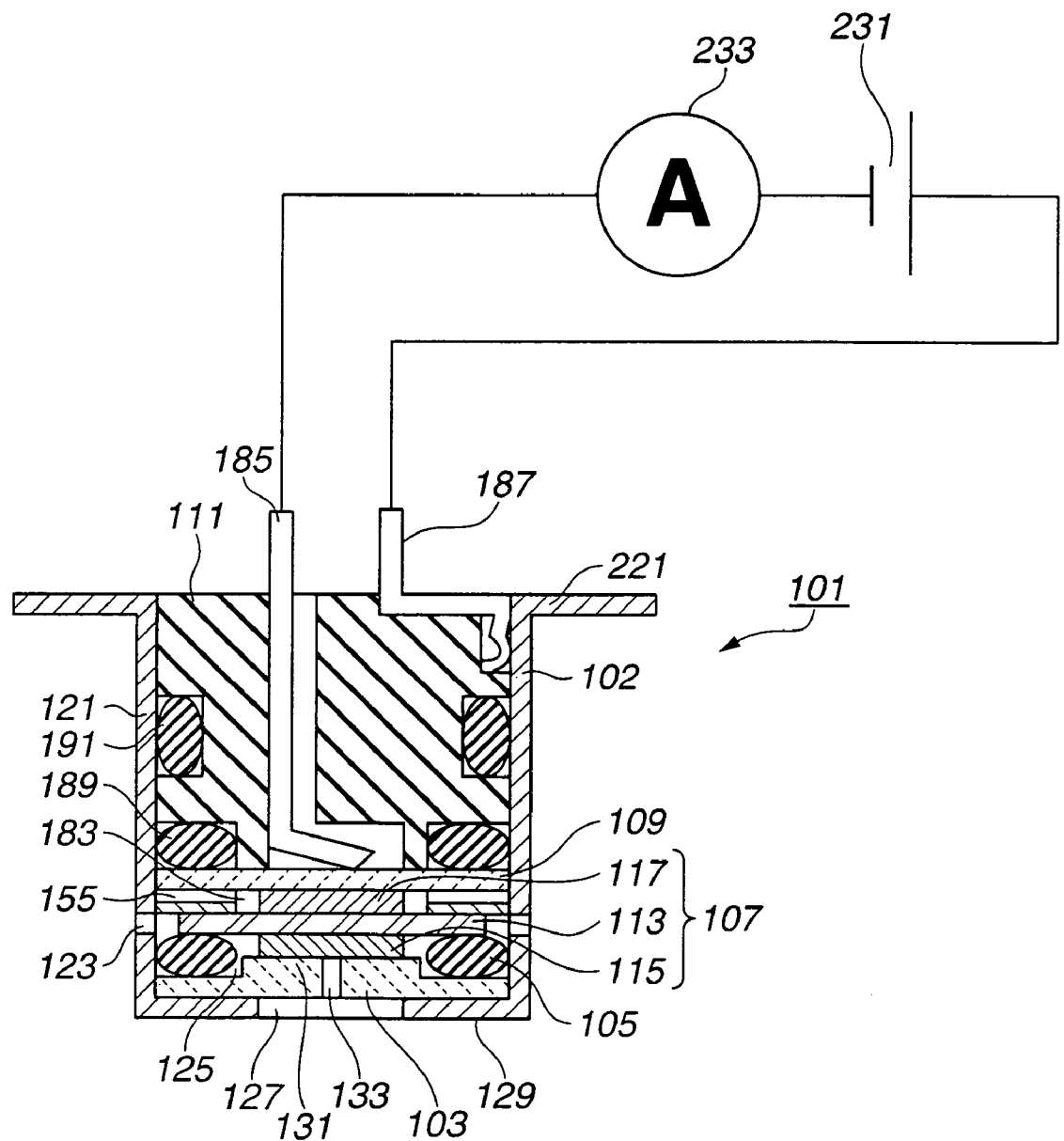
FIG. 9 is a section view of a sensor body of a gas sensor according to a second embodiment of the present invention.
Figure 10:
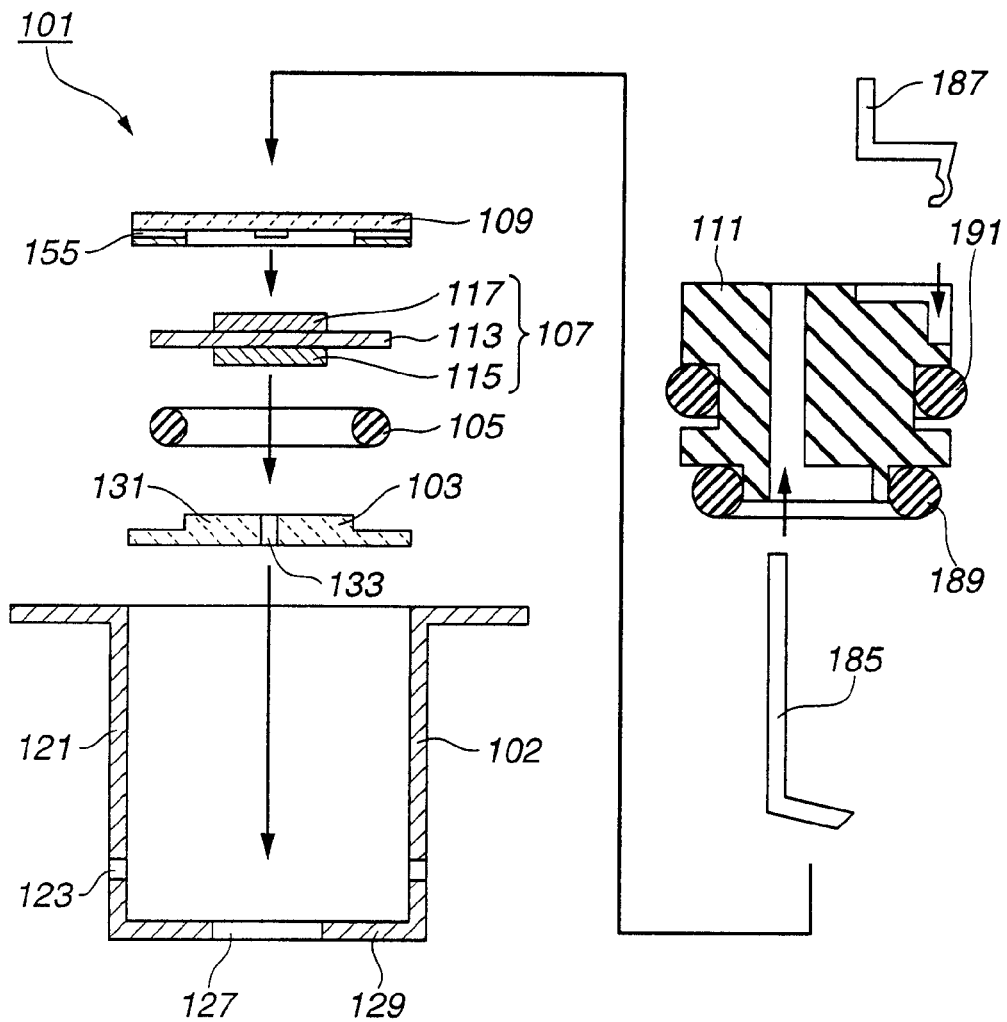
FIG. 10 is an exploded section view of the sensor body of the gas sensor according to the second embodiment of the present invention.

As shown in FIGS. 9 and 10, the hydrogen gas sensor includes a sensor body 101 provided with a metallic casing 102, a sensor element 107, first and second support members 103 and 109, O-rings 105, 189 and 191, a spacer 111 and a pair of negative and positive terminals 185 and 187 to measure the concentration of hydrogen in the gas under measurement.

The casing 102 is formed into a substantially bottomed-cylindrical shape and has a bottom 129 at a front end side thereof, a cylindrical wall 121 and a flange 221 at a base end side thereof, so that the support member 103, the O-ring 105, the sensor element 107, the support member 109 and the spacer 111 are installed in the casing 102 in order of mention (from the front end side) along an axial direction of the casing 102.

The sensor element 107 includes a proton-conductive layer 113 having opposite first and second surfaces and first and second electrodes 115 and 117 disposed in contact with the first and second surfaces of the proton-conductive layer 113, respectively.

Figure 11:
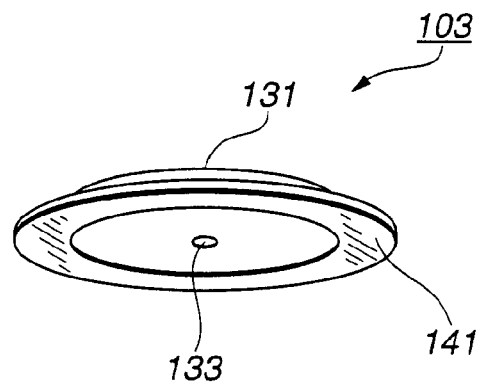
FIG. 11 is a perspective view of a first support member of the gas sensor according to the second embodiment of the present invention.
Figure 12A:
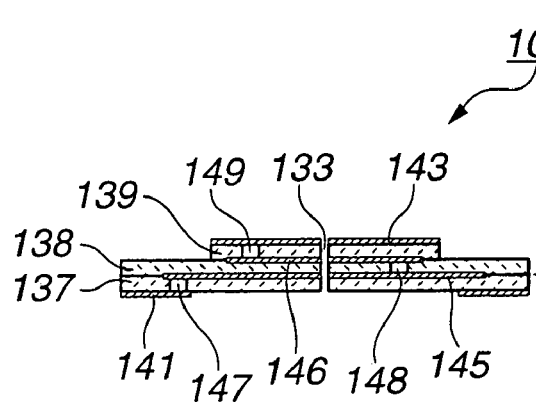
FIG. 12A is a section view of the first support member of the gas sensor according to the second embodiment of the present invention.
Figure 12B:
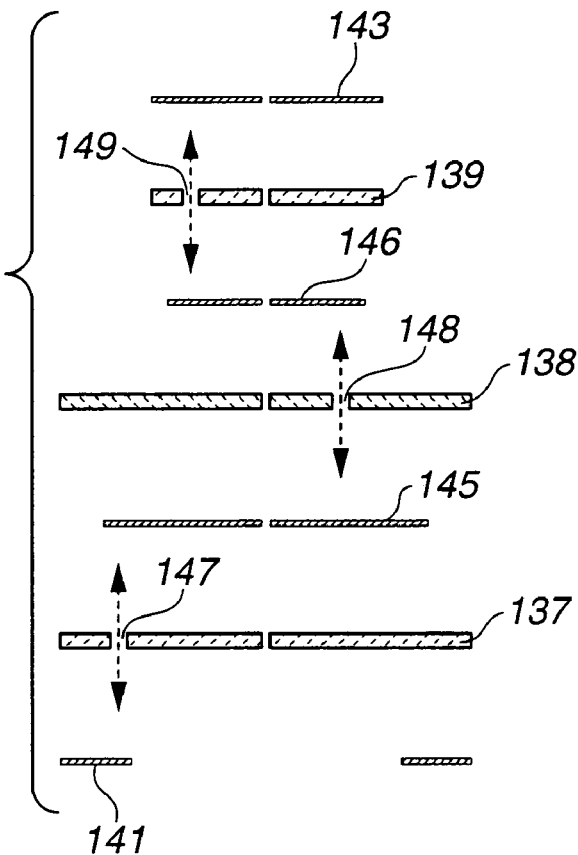
FIG. 12B is an exploded section view of the first support member of the gas sensor according to the second embodiment of the present invention.

As shown in FIGS. 11, 12A and 12B, the first support member 103 is mainly made of a ceramic material and formed into a substantially disc plate. More specifically, the first support member 103 includes disc-shaped first, second and third layers 137, 138 and 139 laminated together, a ring-shaped front end electrode 141 arranged on a front end side of the first layer 137, a disc-shaped base end electrode 143 arranged on a base end side of the third layer 139 and electrically conductive layers 145 and 146 arranged between the first and second layers 137 and 138 and between the second and third layers 138 and 139, respectively. The first, second and third layers 137, 138 and 139 are made of ceramic, such as alumina. The third layer 139 is made smaller in diameter than the first and second layers 137 and 138 so as to define a portion 131 protruded toward the inside (i.e. toward the base end side) at the center of the base end side of the support member 103. Through holes 147, 148 and 149 are formed in the first, second and third layers 137, 138 and 139, respectively, so as to allow axial offsets therebetween, and have inner surfaces plated with an electrically conductive metal (such as platinum) for electrical connections between the front end electrode 141 and the conductive layer 145, between the conductive layers 145 and 146 and between the conductive layer 146 and the base end electrode 143. Further, the first support member 103 is disposed between the bottom 129 of the casing 102 and the front end side of the sensor element 107, with the front end electrode 141 of the first support member 103 brought into contact with the bottom 129 of the casing 102 and with the base end electrode 143 of the protruded portion 131 of the first support member 103 brought into contact with the first electrode 115.

The O-ring 105 is held between the front end side of the sensor element 107 and the base end side of the support member 103 to provide a gas seal between the sensor element 107 and the first support member 103.

With such an arrangement, a measurement chamber 125 enclosing therein the first electrode 115 is defined by the front end side of the sensor element 107, the base end side of the support member 103 (including the protruded portion 131) and the O-ring 105. A gas introduction hole 127 is formed through the bottom 129 of the casing 102, and a small-sized gas diffusion rate limiting hole 133 is formed through the center of the protruded portion 131 of the support member 103 to limit the rate of diffusion of the gas under measurement while introducing the gas into the measurement chamber 125 from the front side of the first support member 103. The measurement chamber 125 thus communicates with the atmosphere of the gas under measurement, i.e., the inside of the pipe through the gas introduction hole 127 and the gas diffusion rate limiting hole 133.

Figure 13:
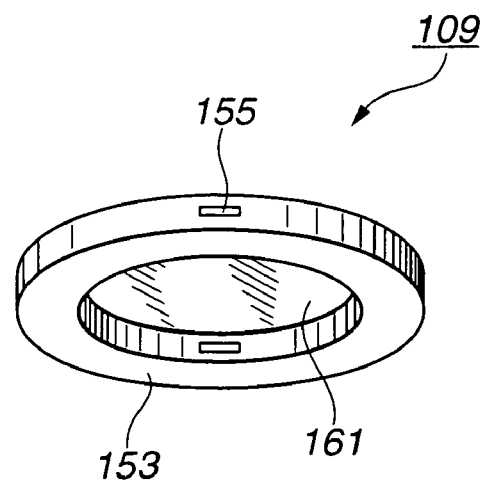
FIG. 13 is a perspective view of a second support member of the gas sensor according to the second embodiment of the present invention.

As shown in FIGS. 13, 14A and 14B, the second support member 109 is mainly made of a ceramic material and formed into a substantially disc plate. More specifically, the second support member 109 includes first to fourth layers 157 to 160 laminated together. The first and second layers are ring-shaped so as to define a recessed portion 153 in the front end side of the support member 109, whereas the third and fourth layers 159 and 160 are disc-shaped. Each of the first to fourth layers 157 to 160 is made of ceramic, such as alumina. The support member 109 further includes a disc-shaped front end electrode 161 arranged on a front end side of the third layer 159, a disc-shaped base end electrode 163 arranged on a base end side of the fourth layer 160 and an electrically conductive layer 165 arranged between the third and fourth layers 159 and 160, as shown in FIGS. 14A and 14B. Through holes 167 and 169 are formed in the third and fourth layers 159 and 169, respectively, so as to allow axial offsets therebetween, and have metal-plated inner surfaces for electrical connections between the front end electrode 161 and the conductive layer 165 and between the conductive layer 165 and the base end electrode 163. The second support member 109 is disposed on the base end side of the sensor element 107 with the second electrode 117 placed in the recessed portion 153 of the support member 109 and brought into contact with the front end electrode 161 of the support member 109.

With this arrangement, a discharge chamber 183 is defined between the front end side of the support member 109 and the base end side of the second electrode 117. Four gas return channels 155 (only two are shown in FIG. 13) are formed in the second layer 158 so as to extend radially outwardly from the recessed portion 153 at locations 90 degrees apart from each other and to be in the form of holes passing laterally through the support member 109. Further, a pair of gas return holes 123 is formed in the cylindrical wall 121 of the casing 102 at locations radially opposing to each other and axially corresponding to the proton-conductive layer 113. The discharge chamber 183 thus communicates with the outside of the casing 102, i.e., the atmosphere of the gas under measurement through the gas return channels 155, a clearance (not shown) between the casing 102 and the outer circumferential portion of the sensor element 107 and the gas return holes 123, as shown in FIG. 9.

Alternatively, the second support member 109 may have a ring-shaped first layer 171, a disc-shaped second layer 173, a disc-shaped third layer 175 and a disc-shaped fourth layer 177 laminated together as shown in FIGS. 15A to 15D. In this alternative, four gas return channels 179 are formed in the second layer 173 at locations 90 degrees apart from each other, so that each of the gas return channels 179 communicates at an inner side thereof with a space 181 surrounded by the first layer 171. Electrodes (not shown) are arranged on the second and fourth layers 173 and 177, respectively. Also, electrically conductive layers (not shown) are arranged between the second and third layers 173 and 175 and between the third and fourth layers 175 and 177. Through holes (not shown) are formed in the respective second, third and fourth layers 173, 175 and 177 for electrical connection between the electrodes through the conductive layers.

As another alternative, the second support member 109 may have the same structure as that of the support member 9 of the first embodiment.

The spacer 111 and the negative and positive terminals 185 and 187 are structurally the same as the spacer 11 and the negative and positive terminals 55 and 59 of the first embodiment, respectively.

The O-ring 189 is held between the support member 109 and the spacer 111 to provide a gas seal between the support member 109 and the spacer 111. Likewise, the O-ring 191 is held between the casing 102 and the spacer 111 to provide a gas seal between the casing 102 and the spacer 111.

Figure 16:
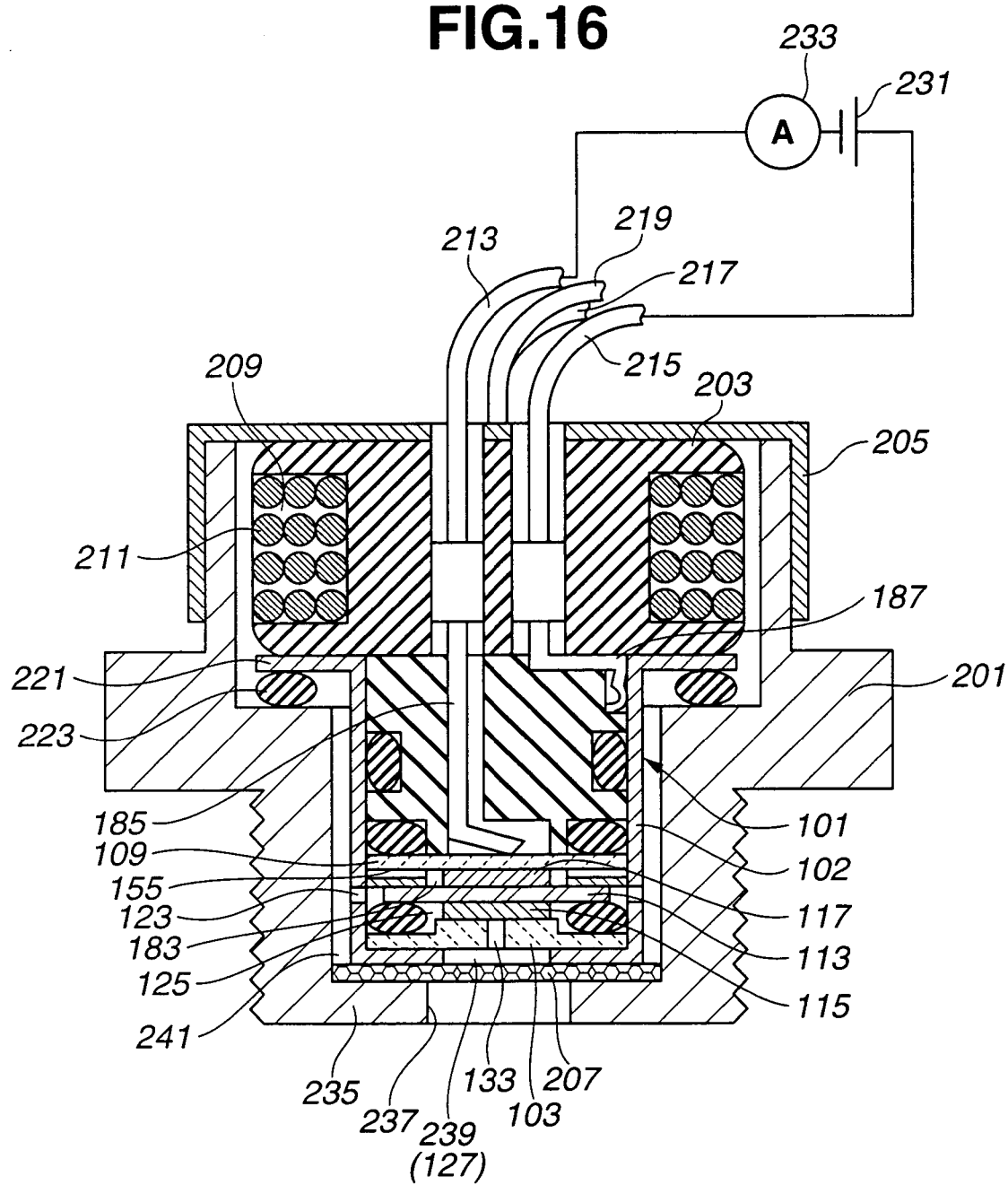
FIG. 16 is a section view of the gas sensor according to the second embodiment of the present invention.
Figure 17:
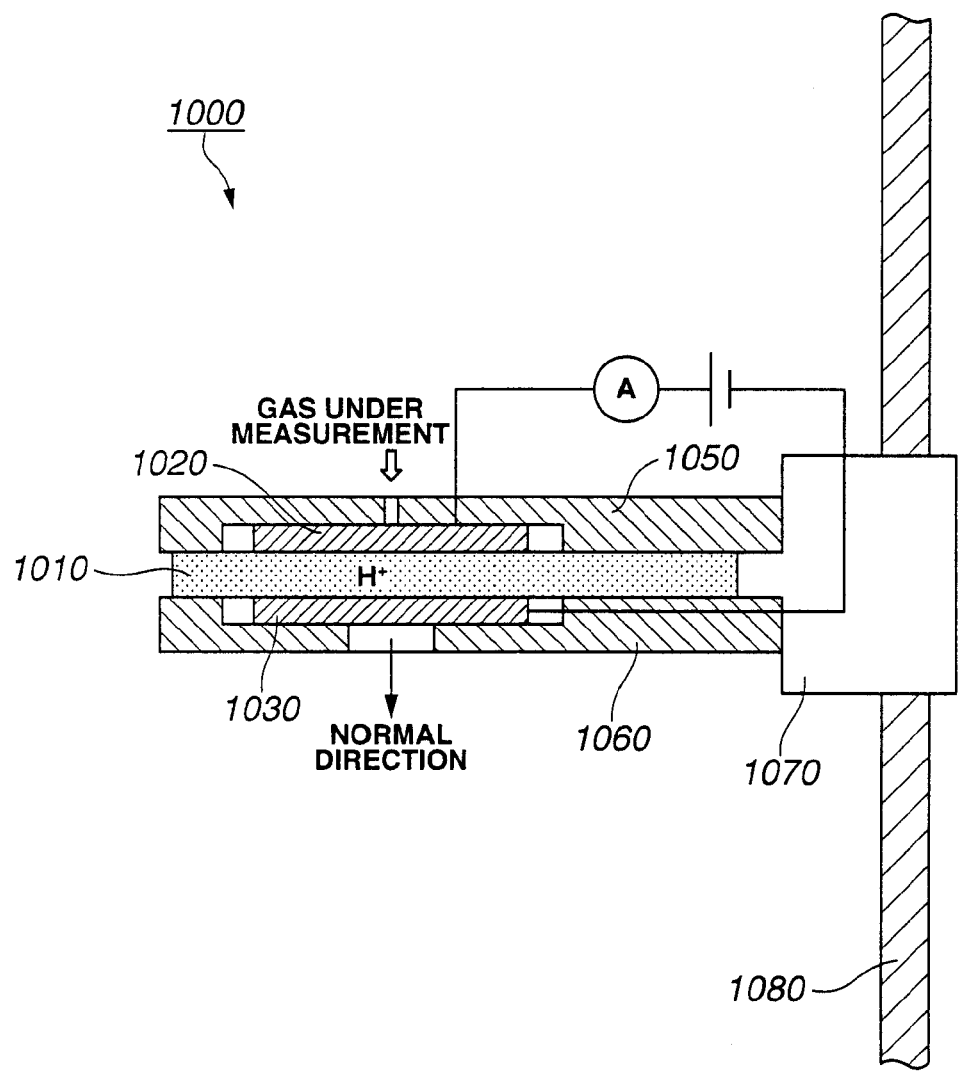
FIG. 17 is a sectional view of a sensor body of a gas sensor according to the earlier technology.

As shown in FIG. 16, the hydrogen gas sensor further includes a metallic sensor housing 201 installing therein the sensor body 101, a grommet 203 pressed against a base end side of the sensor body 101 to hold the sensor body 101 into the sensor housing 201, a metallic cover 205 fitted onto the sensor housing 201, a filter 207, a heater 211, leads 213, 215, 217 and 219 and a O-ring 223.

The sensor housing 201 is formed into a substantially bottomed-cylindrical shape and has a bottom 235 formed with a gas port 237 for introducing therethrough the gas under measurement to the sensor body 101. There is an axial space 241 (hereinafter referred to as a gas return channel) left between an inner cylindrical surface of the sensor housing 201 and an outer surface of the cylindrical wall 121 of the casing 102.

The filter 207 is sandwiched between the bottom 129 of the casing 102 and the bottom 235 of the sensor housing 201. In the second embodiment, a buffering chamber 239 is defined by the gas introduction hole 127 between the filter 207 and the support member 103.

The grommet 203 has a circularly recessed portion 209 formed in an outer circumferential surface thereof, and the heater 211 is wound on the recessed portion 209 of the grommet 203. The structure of the heater 211 is not particularly restricted, as long as the heater 211 is capable of generating heat to prevent condensation inside and outside the hydrogen gas sensor. Alternatively, a resinous bobbin with a wire-wound heater may be used in place of the grommet 203 and the heater 211. The positioning of the heater 221 is not also particularly restricted. Although the heater 221 is provided inside the hydrogen gas sensor in the second embodiment, it is alternatively possible to modify the hydrogen gas sensor in such a manner that the heater 221 is located outside the sensor. However, the heater 221 is desirably disposed outside the pipe so as not to make contact with the gas under the measurement.

The leads 213, 215, 217 and 219 are inserted through axial holes formed in a radial center portion of the grommet 203. The leads 213 and 215 connect the positive and negative terminals 185 and 187 to a direct-current power source 231, respectively, via an ammeter 233. The leads 217 and 219 connect the heater 211 to power source.

The O-ring 223 is held between the flange 221 of the casing 102 and an inner stepped surface of the sensor housing 201 to provide a gas seal between the casing 102 and the sensor housing 201 and thereby prevent the gas from leaking to the base end side of the sensor housing 201.

The above-explained hydrogen gas sensor operates as follows.

Upon the electrical contact between the positive terminal 187 and the cylindrical wall 121 of the casing 102, the electrical contact between the bottom 129 of the casing 102 and the front end electrode 141 of the support member 103, the electrical contact between the base end electrode 143 of the support member 103 and the first electrode 115, the electrical contact between the second electrode 117 and the front end electrode 161 of the support member 109 and the electrical contact between the base end electrode 163 of the support member 109 and the negative terminal 185, the hydrogen gas sensor establishes an electric circuit for applying a direct-current voltage between the first and second electrodes 115 and 117 through the negative and positive terminals 185 and 187 by means of the power source 231.

The gas under measurement flows from the pipe into the measurement chamber 125 through the gas port 237 of the bottom 235 of the sensor housing 201, the filter 207, the buffering chamber 239, and then, the gas diffusion rate limiting hole 133 of the support member 103. By the application of the voltage between the first and second electrodes 115 and 117, hydrogen in the gas under measurement undergoes dissociation, decomposition or reaction within the measurement chamber 125 to generate protons ($H^+$) at the first electrode 115. The generated protons migrate from the first electrode 115 to the second electrode 117 through the proton-conductive layer 113 by the pumping action.

The migration of the protons from the first electrode 115 to the second electrode 117 through the proton-conductive layer 113 causes the flow of an electric current. The ammeter 233 reads the amount of such electric current so that the hydrogen gas sensor determines the concentration of hydrogen in the gas under measurement according to the electric current amount read by the ammeter 233.

The protons, drawn to the second electrode 117, are converted into a return gas (i.e. hydrogen) in the discharge chamber 183. The return gas flows through the gas return channels 155 of the support member 109 and the gas return holes 123 of the casing 102 and becomes discharged out of the casing 102. Then, the return gas flows through the gas return channel 241 to the front end side of the support member 103, passes across the filter 207 and returns to the pipe through the gas port 237.

The hydrogen gas sensor of the second embodiment can be assembled in a manner similar to that of the first embodiment.

The second embodiment thus provides similar effects to those of the first embodiment. For instance, the hydrogen gas sensor of the second embodiment is able to attain higher vibration and impact resistance than that of a conventional one-side-supported gas sensor as the sensor element 107 is supported between the first and second support members 103 and 109 on the bottom 129 of the casing 102 with the first and second surfaces of the proton-conductive layer 113 directed toward the front and base ends of the hydrogen gas sensor, respectively. Further, the sensor body 101 can be assembled easily by installing the first support member 103, the sensor element 107, the second support member 109 and the other sensor components in the casing 102.

The following additional effects can be also provided by the second embodiment.

The first support member 103 with the gas diffusion rate limiting hole 133 is provided between the bottom 129 of the casing 102 and the sensor element 107 and is mainly composed of ceramic. In the event that the metallic casing 102 rusts away, the gas diffusion rate limiting hole 133 can be prevented from rusting to decrease in diameter or become clogged. Even when the gas under measurement has a high humidity, the hydrogen gas sensor of the second embodiment is thus able to measure the hydrogen concentration over the long term.

Furthermore, the first support member 103 has an electrically conductive portion including the front and base end electrodes 141 and 143, the conductive layers 145 and 146 and the though holes 147, 148 and 149. Such an electrically conductive portion formed on and through the first support member 103 allows easy and proper electrical connection of the first electrode 115 to the external power source 231 through the positive terminal 187. As the metallic casing 102 has electrical conductivity, the electrical connection between the first electrode 115 and the positive terminal 187 can be secured easily and assuredly by the metallic casing 102.

The gas return channels 155 are in the form of holes passing laterally outwardly through the second support member 109. Thus, the gas return channels 155 is more resistant to clogging even in such a condition that the grommet 203 pushes the second support member 109, the sensor element 107 and the other sensor components to the first support member 103.

The sensor body 101 and the other sensor components are heated by the heater 211, thereby preventing condensation in the gas return channels 133 and 155 even when the gas under measurement is high in humidity and maintaining the proper performance of the hydrogen gas sensor. In addition, the heater 211 is located outside the pipe and isolated from the front end portion of the sensor body 101 by means of the O-ring 223. The hydrogen gas sensor of the second embodiment can attain a higher level of safety, even when the hydrogen concentration of the gas under measurement is high.

The entire contents of Japanese Patent Application Nos. 2003-024984 (filed on Jan. 31, 2003) and 2003-407825 (filed on Dec. 5, 2003) are herein incorporated by reference.

Although the present invention has been described with reference to specific embodiments of the invention, the invention is not limited to the above-described embodiments. Various modification and variation of the embodiments described above will occur to those skilled in the art in light of the above teaching. The scope of the invention is defined with reference to the following claims.

What is claimed is:

1. A gas sensor for measuring the concentration of a specific gas component in a gas under measurement, comprising:
a gas diffusion rate limiting portion limiting the rate of diffusion of the gas under measurement;
a measurement chamber communicating with an atmosphere of the gas under measurement through the gas diffusion rate limiting portion;
a sensor element having an ion-conductive layer with first and second surfaces, a first electrode disposed in contact with the first surface of the ion-conductive layer within the measurement chamber, and a second electrode disposed in contact with the second surface of the ion-conductive layer and communicating exclusively with the atmosphere of the gas under measurement;
a cylindrical support member installing therein the sensor element with the first and second surfaces of the ion-conductive layer directed toward front and base end sides of the support member, respectively;
a circuit for applying a voltage between the first and second electrodes to cause dissociation, decomposition or reaction of the specific gas component of the gas in the measurement chamber and thereby generates ions at the first electrode, allowing an electric current flow due to migration of the ions from the first electrode to the second electrode through the ion-conductive layer, and determining the concentration of the specific component in the gas under measurement based on the electric current flow;
a gas introduction passage for introducing the gas from the atmosphere of the gas under measurement to the first electrode; and
a gas return passage for returning the gas drawn to the second electrode to the atmosphere of the gas under measurement, said gas return passage extending in a direction from the second electrode to the first electrode.

2. A gas sensor according to claim 1, wherein the gas introduction passage leads to the measurement chamber from the front end side of the support member.

3. A gas sensor according to claim 1, wherein the gas diffusion rate limiting portion is formed in the support member.

4. A gas sensor according to claim 1, further comprising a filter having water repellency and air permeability and arranged between the gas diffusion rate limiting portion and the atmosphere of the gas under measurement.

5. A gas sensor according to claim 1, wherein the ion-conductive layer is a proton-conductive layer so that the gas sensor measures the concentration of hydrogen in the gas under measurement.

6. A gas sensor according to claim 1, wherein the gas sensor is designed to be fixed to a pipe through which the gas under measurement flows.

7. A gas sensor for measuring the concentration of a specific gas component in a gas under measurement, comprising:
   a gas diffusion rate limiting portion limiting the rate of diffusion of the gas under measurement;
   a measurement chamber communicating with an atmosphere of the gas under measurement through the gas diffusion limiting portion;
   a sensor element provided with an ion-conductive layer having first and second surfaces directed to front and base ends of the gas sensor, respectively, a first electrode disposed in contact with the first surface of the ion-conductive layer within the measurement chamber, and a second electrode disposed in contact with the second surface of the ion-conductive layer and communicating exclusively with the atmosphere of the gas under measurement:
   first and second support members located on front and base end sides of the sensor element, respectively, to support the sensor element between the first and second support members;
   a circuit for applying a voltage between the first and second electrodes to cause dissociation, decomposition or reaction of the specific component of the gas in the measurement chamber and thereby generate ions at the first electrode, allowing an electric current flow due to migration of the ions from the first electrode to the second electrode through the ion-conductive layer, and determining the concentration of the specific component in the gas under measurement based on the electric current flow;
   a gas introduction passage for introducing the gas from the atmosphere of the gas under measurement to the first electrode; and
   a gas return passage for returning the gas drawn to the second electrode to the atmosphere of the gas under measurement, extending in a direction from the second electrode to the first electrode,
   wherein the gas introduction passage has a gas introduction hole formed in the first support member such that the gas introduction passage leads to the measurement chamber from a front end side of the first support member.

8. A gas sensor according to claim 7, the gas return passage including:
   a first gas return channel extending laterally outwardly in the second support member; and
   a second gas return channel connected with the first gas return channel and extending to a front end side of the first support member.

9. A gas sensor according to claim 7, wherein the gas diffusion rate limiting portion is formed in the first support member.

10. A gas sensor according claim 7, wherein the first support member is formed into a cylindrical shape and installs therein the sensor element and optionally the second support member.

11. A gas sensor according to claim 7, wherein the first support member is mainly made of a ceramic material.

12. A gas sensor according to claim 11, wherein the first support member has an electrically conductive portion connected to the first electrode.

13. A gas sensor according to claim 7, further comprising an elastic member pushing the second support member and the sensor element to the first support member.

14. A gas sensor according to claim 7, further comprising a filter having water repellency and air permeability and arranged between the gas diffusion rate limiting portion and the atmosphere of the gas under measurement.

15. A gas sensor according to claim 7, wherein the ion-conductive layer is a proton-conductive layer so that the gas sensor measures the concentration of hydrogen in the gas under measurement.

16. A gas sensor according to claim 7, wherein the gas sensor is designed to be fixed to a pipe through which the gas under measurement flows.

17. A gas sensor for measuring the concentration of a specific gas component in a gas under measurement, comprising:
   a gas diffusion rate limiting portion limiting the rate of diffusion of the gas under measurement;
   a measurement chamber communicating with an atmosphere of the gas under measurement through the gas diffusion limiting portion;
   a sensor element having an ion-conductive layer with first and second surfaces, a first electrode disposed in contact with the first surface of the ion-conductive layer within the measurement chamber, and a second electrode disposed in contact with the second surface of the ion-conductive layer and communicating exclusively with the atmosphere of the gas under measurement:
   means for supporting the sensor element in such a manner the first and second surface of the ion-conductive layer are directed toward front and base ends of the gas sensor, respectively;
   a circuit for applying a voltage between the first and second electrodes to cause dissociation, decomposition or reaction of the specific component of the gas in the measurement chamber and thereby generate ions at the first electrode, allowing an electric current flow due to migration of the ions from the first electrode to the second electrode through the ion-conductive layer, and determining the concentration of the specific component in the gas under measurement based on the electric current flow;
   a gas introduction passage for introducing the gas from the atmosphere of the gas under measurement to the first electrode; and
   a gas return passage for returning the gas drawn to the second electrode to the atmosphere of the gas under measurement, said gas return passage extending in a direction from the second electrode to the first electrode.

18. A gas sensor according to claim 17, wherein the gas sensor is designed to be fixed to a pipe through which the gas under measurement flows.

19. A gas sensor for measuring the concentration of a specific gas component in a gas under measurement, comprising:
   a gas diffusion rate limiting portion limiting the rate of diffusion of the gas under measurement;
   a measurement chamber communicating with an atmosphere of the gas under measurement through the gas diffusion limiting portion;
   a sensor element provided with an ion-conductive layer having first and second surfaces directed to front and base ends of the gas sensor, respectively, a first electrode disposed in contact with the first surface of the ion-conductive layer within the measurement chamber, and a second electrode disposed in contact with the second surface of the ion-conductive layer and communicating exclusively with the atmosphere of the gas under measurement:

first and second support members located on front and base end sides of the sensor element, respectively, to support the sensor element between the first and second support members; and a circuit for applying a voltage between the first and second electrodes to cause dissociation, decomposition or reaction of the specific component of the gas in the measurement chamber and thereby generate ions at the first electrode, allowing an electric current flow due to migration of the ions from the first electrode to the second electrode through the ion-conductive layer, and determining the concentration of the specific component in the gas under measurement based on the electric current flow, the second support member having:

at least two ceramic layers laminated to each other;

a front end electrode arranged at a front end side of the second support member;

a base end electrode arranged at a base end side of the second support member;

at least one electrically conductive layer, each of which is arranged between adjacent two of the ceramic layers; and through holes formed in the respective ceramic layers so as to allow offset therebetween and to provide electrical connection between the front and base end electrodes through said at least electrically conductive layer.

* * * * *